(12) United States Patent
Lee et al.

(10) Patent No.: US 10,442,634 B2
(45) Date of Patent: Oct. 15, 2019

(54) TABLET INSPECTION APPARATUS

(71) Applicant: ENCLONY INC, Seoul (KR)

(72) Inventors: Kyung-Ho Lee, Seoul (KR); Byung-In Kim, Seoul (KR)

(73) Assignee: ENCLONY INC, Seoul (KR)

( * ) Notice: Subject to any disclaimer, the term of this patent is extended or adjusted under 35 U.S.C. 154(b) by 44 days.

(21) Appl. No.: 15/567,119

(22) PCT Filed: Apr. 14, 2016

(86) PCT No.: PCT/KR2016/003887
§ 371 (c)(1),
(2) Date: Oct. 17, 2017

(87) PCT Pub. No.: WO2016/167567
PCT Pub. Date: Oct. 20, 2016

(65) Prior Publication Data
US 2018/0148273 A1    May 31, 2018

(30) Foreign Application Priority Data
Apr. 17, 2015  (KR) .................... 10-2015-0054636

(51) Int. Cl.
*B65G 47/52*   (2006.01)
*B65G 31/04*   (2006.01)
(Continued)

(52) U.S. Cl.
CPC ............ *B65G 47/525* (2013.01); *B07C 5/365* (2013.01); *B65G 29/00* (2013.01); *B65G 31/04* (2013.01); *B65G 47/14* (2013.01); *B65G 47/1407* (2013.01); *B65G 47/1457* (2013.01); *B65G 49/00* (2013.01); *G01N 21/9508* (2013.01); *B07C 5/3422* (2013.01); *B65G 2201/027* (2013.01)

(58) Field of Classification Search
CPC .. B07C 5/365; B07C 5/3422; G01N 21/9508; B65G 47/525; B65G 47/1457;
(Continued)

(56) References Cited

U.S. PATENT DOCUMENTS 4,354,602 A * 10/1982 Miyoshi .................... B07C 5/36
                                                         209/545
4,582,201 A *  4/1986 Taniguchi ................. B07C 5/36
                                                         198/377.04

(Continued)

FOREIGN PATENT DOCUMENTS

JP    03-042415 A    2/1991
JP    11-51873 A     2/1999
(Continued)

OTHER PUBLICATIONS

International Search Report and Written Opinion for corresponding Patent Application No. PCT/KR2016/003887 dated Jul. 22, 2016.

*Primary Examiner* — Joseph C Rodriguez
*Assistant Examiner* — Kalyanavenkateshware Kumar
(74) *Attorney, Agent, or Firm* — Renner, Otto, Boisselle & Sklar, LLP

(57) ABSTRACT

A tablet inspection apparatus includes a supply unit including a rotary plate inclinedly disposed, and a transfer plate having a downwardly inclined surface, inclined outwardly on the same level as top dead center of the rotary plate while rotating with the rotary plate around the rotary plate, a first rotary unit inclinedly disposed with respect to the supply unit, and formed such that suction force is applied in a certain section in a circumferential direction, and a second rotary unit installed on one side of the first rotary unit, and formed such that suction force is applied in a certain section in a circumferential direction.

7 Claims, 3 Drawing Sheets

(51) Int. Cl.
  *B65G 47/14* (2006.01)
  *B65G 49/00* (2006.01)
  *B07C 5/36* (2006.01)
  *G01N 21/95* (2006.01)
  *B65G 29/00* (2006.01)
  *B07C 5/342* (2006.01)

(58) Field of Classification Search
  CPC .... B65G 47/1407; B65G 47/14; B65G 29/00; B65G 31/04; B65G 49/00; B65G 2201/027
  See application file for complete search history.

(56) References Cited

U.S. PATENT DOCUMENTS

| | | | |
|---|---|---|---|
| 4,673,077 A * | 6/1987 | Taniguchi | B65G 47/1457 198/393 |
| 4,757,382 A * | 7/1988 | Kaziura | B65G 21/2036 198/689.1 |
| 5,661,249 A * | 8/1997 | Rupp | B07C 5/36 73/45 |
| 6,079,284 A | 6/2000 | Yamamoto et al. | |
| 6,741,731 B1 * | 5/2004 | Yamamoto | G01N 21/9508 382/141 |
| 2007/0289660 A1 * | 12/2007 | Aylward | B65B 5/103 141/18 |
| 2012/0293649 A1 * | 11/2012 | Nygaard | G01N 21/9508 348/91 |
| 2013/0022250 A1 * | 1/2013 | Nygaard | A61J 3/007 382/128 |

FOREIGN PATENT DOCUMENTS

| | | | | |
|---|---|---|---|---|
| JP | 2005-007273 A | | 1/2005 | |
| JP | 2005-289584 A | | 10/2005 | |
| JP | 2009-023844 | * | 2/2009 | ............. B65G 47/14 |
| JP | 2009-023844 A | | 2/2009 | |
| KR | 10-1404868 B1 | | 6/2014 | |

* cited by examiner

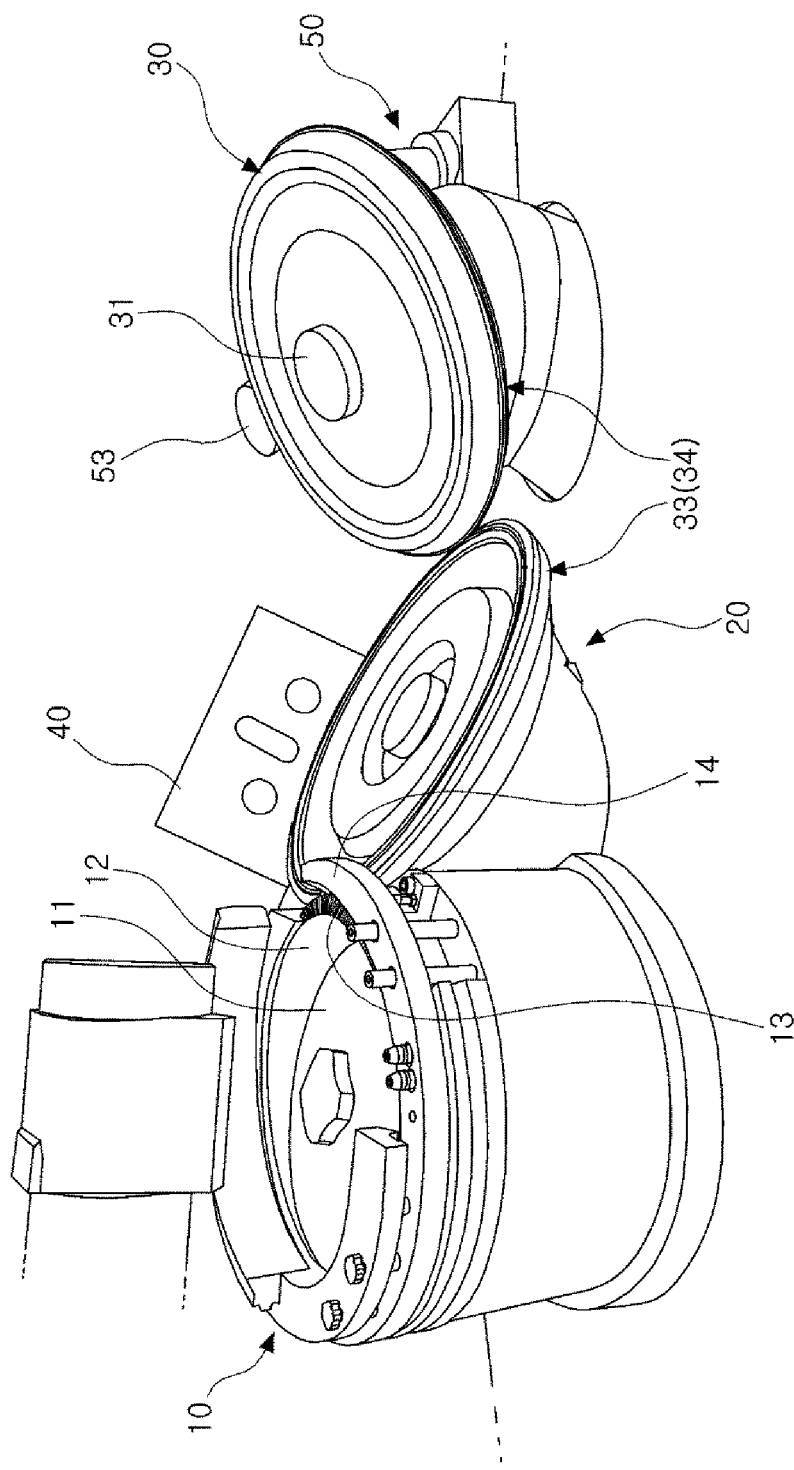
[FIG. 1]

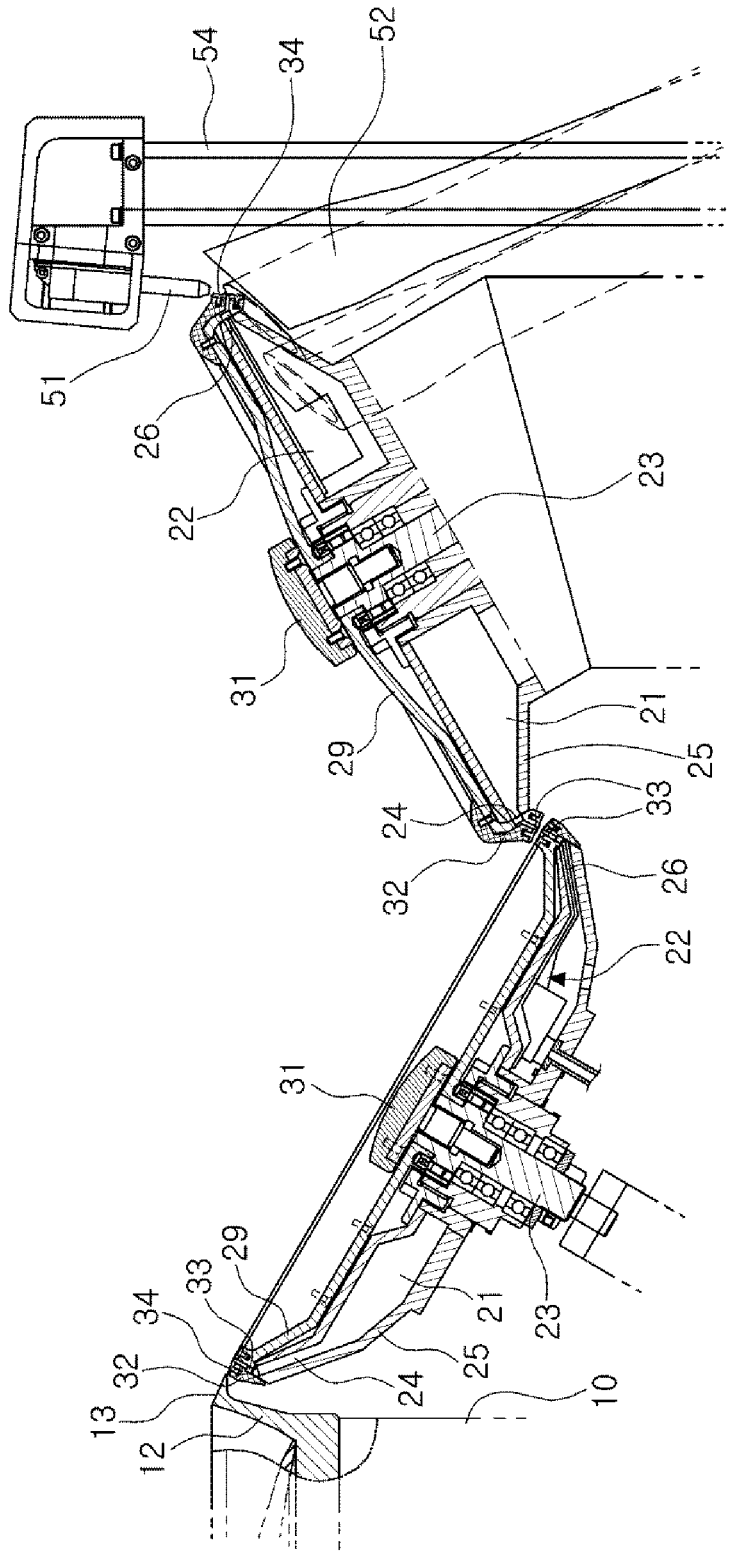
[FIG. 2]

[FIG. 3]
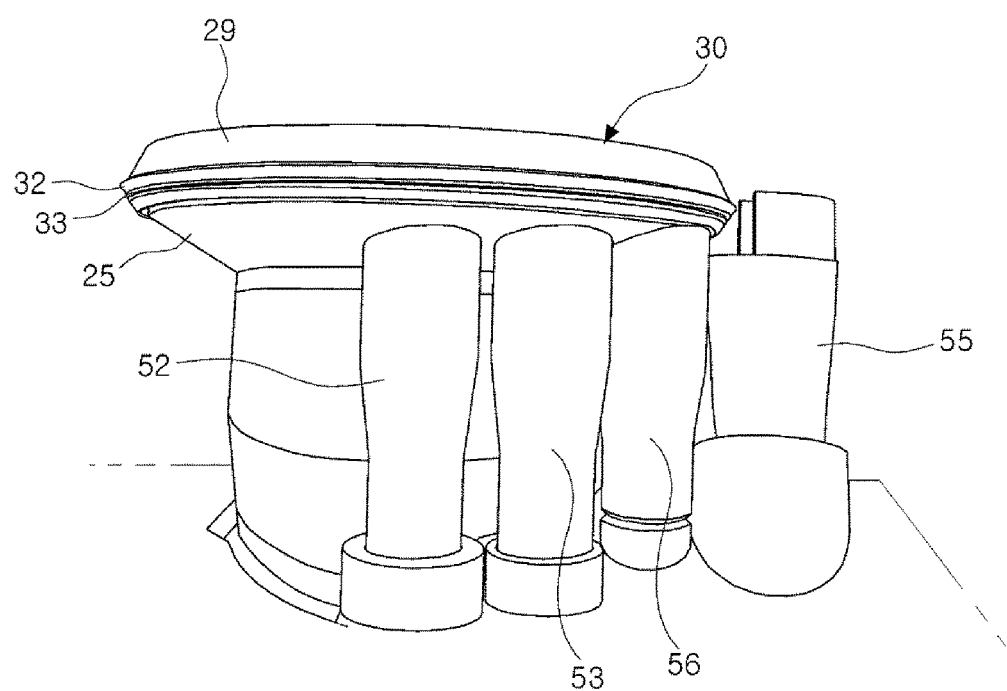

TABLET INSPECTION APPARATUS

TECHNICAL FIELD

The present disclosure relates to a tablet inspection apparatus for inspecting an appearance of a tablet while suction-holding and transferring the tablet, and more particularly, to a tablet inspection apparatus reliably and smoothly transferring a tablet while being compactly configured.

BACKGROUND ART

According to the related art, since a capsule or a tablet having an elliptical or circular cross-section may be produced in large quantities through an automated process, a defect is commonly generated during a discharging process, rather than defects caused due to components or dosages thereof.

Accordingly, a process of inspecting an external defect such as a crack, partial damage, deformation, or a printing defect, caused by adhesion of a foreign substance or contamination, contact between tablets, impacts, or the like, has been required.

A process of inspecting an appearance of a tablet has been changing from a visual inspection performed by an operator to an automatic inspection using an automatic inspection apparatus. Various types of automatic inspection apparatuses for such automatic inspection have been proposed.

In a case of automatically inspecting a tablet using an automatic inspection apparatus, a tablet is imaged by a camera while the tablet is being transferred, so an image of one side surface of the tablet is obtained. Moreover, while a tablet's aspect is reversed and the tablet is transferred, the other side surface of the tablet is imaged by a camera. Thereafter, images of one side, a front surface, and the other side, a rear surface, of the tablet are processed, so the presence or absence of a defect may be inspected, a process described above was adopted in the related art.

An example of such a technique is disclosed in Japanese Patent Application Laid-Open No. 11-51873. The example is related to a tablet appearance inspection apparatus, and components thereof from a hopper to a feeder, a side surface inspection drum, an aspect conversion drum, a surface inspection drum, a rear surface inspection drum, and a discharge nozzle, are arranged vertically (in a height direction of the tablet appearance inspection apparatus).

Thus, the tablet appearance inspection apparatus is designed to be high on the whole, so that it is unnecessarily large in size. When an operator directly provides a tablet to be inspected to a hopper, the operator should stand in an elevated position, so a problem in which a worker's workload and the risk of accidents are increased may occur.

DISCLOSURE

Technical Problem

An aspect of the present disclosure may provide a tablet inspection apparatus reliably and smoothly transferring a tablet and being compactly configured.

Technical Solution

According to an aspect of the present disclosure, a tablet inspection apparatus includes: a supply unit including a rotary plate inclinedly disposed, and a transfer plate having a downwardly inclined surface, inclined outwardly at the same level as top dead center of the rotary plate while rotating with the rotary plate around the rotary plate; a first rotary unit inclinedly disposed with respect to the supply unit, and formed such that suction force is applied in a certain section in a circumferential direction; and a second rotary unit installed on one side of the first rotary unit, and formed such that suction force is applied in a certain section in a circumferential direction.

Advantageous Effects

According to an exemplary embodiment in the present disclosure, rotary units, formed such that suction force is applied, are disposed to be inclined with respect to a supply unit and with respect to each other, so a tablet may be reliably and smoothly transferred and a size in a height direction of a tablet inspection apparatus may be reduced for a compact configuration.

DESCRIPTION OF DRAWINGS

FIG. 1 is a perspective view illustrating a tablet inspection apparatus according to an exemplary embodiment.

FIG. 2 is a cross-sectional view illustrating a positional relationship between a first rotary unit and a second rotary unit in the tablet transfer device according to an exemplary embodiment illustrated in FIG. 1.

FIG. 3 is a side perspective view illustrating a positional relationship between a second rotary unit and a discharge unit.

BEST MODE FOR INVENTION

Hereinafter, preferred embodiments of the present disclosure will be described with reference to the accompanying drawings. In adding reference numerals to the elements of the respective drawings, it should be noted that the same elements have the same or similar reference numerals, even when illustrated in different drawings. In the following description, detailed descriptions of known functions and configurations incorporated herein will be omitted when it is determined that the gist of the present invention may be rendered unclear by the inclusion thereof.

FIG. 1 is a perspective view illustrating a tablet inspection apparatus according to an exemplary embodiment, while FIG. 2 is a cross-sectional view illustrating a positional relationship between a first rotary unit and a second rotary unit in the tablet transfer device according to an exemplary embodiment illustrated in FIG. 1.

As illustrated in the drawings, a tablet inspection apparatus according to an exemplary embodiment may include a supply unit 10 having a rotary plate 11 inclinedly disposed, and a transfer plate 12 having a downwardly inclined surface 13 inclined outwardly on the same level as top dead center of the rotary plate while rotating with the rotary plate around the rotary plate; a first rotary unit 20 inclinedly disposed with respect to the supply unit, and formed such that suction force is applied in a certain section in a circumferential direction; and a second rotary unit 30 installed on one side of the first rotary unit, and formed such that suction force is applied in a certain section in a circumferential direction.

The supply unit 10 has the rotary plate 11 inclinedly disposed, and the transfer plate 12 disposed on a side of an outer diameter of the rotary plate on the same horizontal plane as top dead center of the rotary plate and rotating. When the rotary plate rotates, a tablet supplied to the rotary plate from a hopper (not shown) is moved toward the transfer plate in a side of an outer diameter by centrifugal force, and is then sequentially moved toward the first rotary unit 20, which is inclined, due to rotation of the transfer plate.

The transfer plate 12 has the downwardly inclined surface 13, which is downwardly inclined, in a radially outward direction. In addition, a guide portion 14, guiding a tablet, transferred while being aligned in the downwardly inclined surface, to be discharged toward the first rotary unit 20 by centrifugal force, may be further prepared in an outer circumferential surface of the transfer plate. The downwardly inclined surface and the guide portion allow the tablet, having been supplied, to be disposed in a line in a circumferential direction.

In each of the first rotary unit 20 and the second rotary unit 30, a vacuum pressure area 21 and an atmospheric pressure or positive pressure region 22 are divided therein, and a concave groove 33 including a suction-holding section corresponding to the vacuum pressure area or a discharge section corresponding to the atmospheric pressure or positive pressure region is prepared on a circumferential surface. Thus, a tablet is held by providing suction force to the tablet in one section, and a tablet is separated by applying atmospheric pressure or positive pressure to the tablet in the other section.

The first rotary unit 20 and the second rotary unit 30 may be preferably installed to be rotated in opposite directions. For example, when the first rotary unit rotates clockwise, the second rotary unit rotates counterclockwise. However, an exemplary embodiment is not limited to rotation in the opposite directions, but the first rotary unit and the second rotary unit may rotate in the same direction.

In further detail, the first rotary unit 20 or the second rotary unit 30 used herein may include a fixed disk 25 in which a rotating shaft 23 is installed to pass therethrough, forming the vacuum pressure area 21, to which vacuum pressure is at least partially applied, therein, and provided with a suction hole 24 in communication with at least the vacuum pressure area; and a rotary disk 29 combined with the rotating shaft to be rotated, and in which the concave groove 33 to be in communication with the vacuum pressure area is formed on a circumferential surface.

In the fixed disk 25, the rotating shaft 23 passes therethrough, a negative pressure device such as an external vacuum suction device, a vacuum pump, or the like is connected thereto in order to form the vacuum pressure area 21, and at least one blocking block (not shown) dividing the vacuum pressure area from a remaining area is provided therein.

The fixed disk 25 is surrounded by the blocking block in order to form the atmospheric pressure or positive pressure region 22, to which atmospheric pressure or positive pressure is applied, in a portion of the remaining area to which vacuum pressure is not applied, and may be in communication with ambient air or may be connected to a positive pressure device such as an external air pump, or the like.

Moreover, the atmospheric pressure or positive pressure region 22 is in communication with a discharge hole 26 formed in a portion of a front end surface in a circumferential direction of the fixed disk 25.

Thus, vacuum pressure or suction force is formed in the suction hole 24 of the fixed disk 25, and atmospheric pressure or positive pressure is formed in the discharge hole 26. As the fixed disk is fixed, the vacuum pressure and the atmospheric pressure or positive pressure are formed in a constant position.

The rotary disk 29 is coupled to the rotating shaft 23 by a connecting screw 31, and the rotating shaft is connected to a driving portion, for example a motor, not illustrated, or the like, and is rotated. The rotary disk may be formed to cover one surface of the fixed disk 25, an outer circumferential tip portion is bent toward the fixed disk to form an extended portion 32, and the extended portion 32 allows a front end surface of the fixed disk to be shielded.

The concave groove 33 is formed in the extended portion 32, and is disposed along a circumferential surface of the rotary disk 29. A plurality of communication holes (not shown), in communication with the suction hole 24 or the discharge hole 26 along a side wall of the concave groove, may be formed at regular intervals.

In addition, a pair of seating members 34, opposing each other with a predetermined gap therebetween, are attached to both sides of an opening of the concave groove 33, that is, tips of an opening between both side walls of the concave groove. The seating members are formed of an elastic material, for example, rubber, or the like. Thus, when the seating members are in contact with a tablet, the tablet may be prevented from being damaged by impacts.

As described above, the rotary disk 29 rotates while covering one surface of the fixed disk 25, vacuum pressure is applied to an inside of the concave groove in a position in communication with the suction hole 24 of the fixed disk through communication holes of the concave groove 33 formed on a circumferential surface along the extended portion 32 of the rotary disk, and atmospheric pressure or positive pressure is applied to an inside of the concave groove in a position in communication with the discharge hole 26 of the fixed disk.

Thus, in the suction-holding section to which vacuum pressure is applied, a tablet is supported while being held on the seating member 34 located in the concave groove 33 prepared along a circumferential surface of the rotary disk 29, and is sequentially rotated with the rotary disk to be transferred. A position of the tablet, held on the seating member, does not necessarily correspond to a position of the communication hole, and the tablet may be arranged in a line in the concave groove on a circumferential surface at irregular intervals.

Next, when the tablet reaches a desired position, that is, an end point of the suction-holding section to which vacuum pressure is applied, or a starting point of the discharge section to which atmospheric pressure or positive pressure is applied, instead of vacuum pressure, the tablet is separated from the seating member 34 to be discharged. In this case, a level of the positive pressure is preferably set to be greater than a level of the vacuum pressure.

In the first rotary unit 20, the concave groove 33 or the seating member 34 is disposed in an upper surface of the extended portion 32. In this case, a plane, formed by both tips of an opening of the concave groove, or a plane, formed by both upper surfaces of the seating member, forms the same plane as the downwardly inclined surface 13 of transfer plate 12 of the supply unit 10.

The same plane preferably has an angle of inclination of about 20° to 40° with respect to a horizontal plane, and most preferably has an angle of inclination of 25°. When the angle of inclination is less than 20°, a slope is significantly gentle, so the tablet is limited in slidingly-moving along the downwardly inclined surface 13. On the other hand, when the angle of inclination exceeds 40°, for example, in a case of a tablet having an edge, a tablet may be frequently overturned, so the tablet may not be inspected in a desired aspect.

As described above, the first rotary unit 20 holds the tablet, slidingly-moving to be discharged from the supply unit 10, in a location below the tablet, so the tablet may be reliably held and then smoothly transferred.

In the second rotary unit 30, the concave groove 33 or the seating member 34 is disposed in a lower surface or a downwardly inclined surface of the extended portion 32. In this case, a plane, formed by both tips of an opening of the concave groove of the first rotary unit 20, and a plane, formed by both tips of an opening of the concave groove of the second rotary unit, are disposed parallel to each other, and the concave grooves thereof pass through each other while opposing each other at a point. Alternatively, a plane, formed by both upper surfaces of seating members of the first rotary unit, and a plane, formed by both upper surfaces of seating members of the second rotary unit, are disposed parallel to each other, and the seating members thereof pass through each other while opposing each other at a point.

Although the second rotary unit 30 is inclinedly disposed with respect to the first rotary unit 20, it is sufficient that planes, formed by both tips of an opening of concave grooves 33, are disposed parallel to each other, or planes, formed by both upper surfaces of seating members 34, are disposed parallel to each other. Thus, as a suction-holding surface of a tablet, held by the first rotary unit, is accurately reversed, the suction-holding surface is provided as an exposed surface in the second rotary unit.

Thus, in FIGS. 1 and 2, an upper surface of the first rotary unit 20 and an upper surface of the second rotary unit 30 are illustrated as being inclined with respect to each other so as to have a substantially V-shaped positional relationship, by way of example, but an exemplary embodiment is not limited thereto.

As described above, the supply unit 10, an upper surface of the first rotary unit 20, and the second rotary unit 30 may be disposed to be inclined with respect to each other, which has an advantage in that a size of a device in a height direction may be reduced for a compact configuration.

An imaging unit 40, formed of a combination of cameras capturing an image at different angles while being installed on one side of each of the first rotary unit 20 and the second rotary unit 30, may be installed. Thus, in the tablet inspection apparatus according to an exemplary embodiment, while a tablet, sequentially supplied in a line through the supply unit 10, is held by the first rotary unit 20 and the second rotary unit 30 to be transferred, an appearance of the tablet is imaged with cameras.

FIG. 3 is a side perspective view illustrating a positional relationship between a second rotary unit and a discharge unit. As illustrated in FIGS. 2 and 3, the tablet inspection apparatus according to an exemplary embodiment may further include a discharge unit 50 disposed in a lower portion of one side of the second rotary unit 30.

The discharge unit 50 may discharge a tablet by separating a satisfactory product from a defective product, among tablets transferred by the second rotary unit 30, according to a result of determination of pass and fail of an appearance of each tablet, obtained from images obtained in the imaging unit 40.

As an example, the discharge unit 50 may include at least one air sprayer 51, at least one defective product outlet 53, and a satisfactory product outlet 55. According to a result of determination of pass and fail in a control unit not illustrated, the air sprayer 51 sprays air onto a defective product, among tablets transferred by the second rotary unit 30, to allow the defective product to be dropped from the second rotary unit.

In this case, the discharge unit 50 may further include an air sprayer 51 and an inspection missed product outlet 52. The air sprayer 51 sprays air onto an inspection missed product, transferred by the second rotary unit 30 due to lack of determination of pass and fail of an appearance of a tablet, to allow the inspection missed product to be dropped from the second rotary unit.

In addition, the discharge unit 50 may further include an air sprayer 51 and a missing product outlet 56. The air sprayer 51 sprays air onto a missing product, transferred by the second rotary unit 30 while not being dropped even when the missing product is a defective product or an inspection missed product of which determination of pass and fail is missing, to allow the missing product to be dropped from the second rotary unit. A sensor for sensing a missing product may be further installed.

As illustrated in FIG. 2, the air sprayer 51 may be installed near an upper right portion of the second rotary unit 30 through a medium of a separate support bracket 54.

Thus, the inspection missed product outlet 52, the defective product outlet 53, or the missing product outlet 56 allows an inspection missed product or a defective product, dropped from the concave groove 33 or the seating member 34 of the second rotary unit 30 by the air sprayer 51, to be separated and discharged.

Meanwhile, according to a result of determination of pass and fail in a control unit, the satisfactory product outlet 55 may receive and discharge a satisfactory product entering a discharge section in communication with the atmospheric pressure or positive pressure region 22 while being held by the second rotary unit 30 and being transferred. The satisfactory product outlet 55 may separate and discharge the satisfactory product discharged from the concave groove 33 or the seating member 34 of the second rotary unit.

Hereinafter, an operation of a tablet inspection apparatus according to an exemplary embodiment will be briefly described.

After a tablet supplied in bulk is arranged in a line in a circumferential direction by centrifugal force applied by the rotary plate 11 in the supply unit 10, the tablet is supplied to the transfer plate 12 one-by-one to be transferred.

Next, the tablet may sequentially slidingly-move to the first rotary unit 20 which is inclinedly located on the same plane as the downwardly inclined surface 13 of the transfer plate 12. The first rotary unit 20, allowing the tablet to be held by the seating member 34 located in the concave groove 33, rotates while being inclined, thereby sequentially transferring the tablet.

In addition, in a portion where the second rotary unit 30 is located to be close to the first rotary unit 20 by a minimum distance, positive pressure or atmospheric pressure, greater than vacuum pressure, is applied to the tablet from the first rotary unit, so the tablet in a reversed state is held by the second rotary unit. The second rotary unit in which the tablet is held by the seating member 34 of the concave groove 33 rotates, thereby sequentially transferring the tablet.

Moreover, the imaging unit 40 formed of at least one or more cameras is disposed in a circumferential direction of each of the first rotary unit 20 and the second rotary unit 30, thereby imaging an appearance of the tablet. A control unit determines pass and fail of the tablet from images obtained by the imaging unit 40, and the tablet may be discharged from the second rotary unit to the defective product outlet 53 or the satisfactory product outlet 55 according to a result thereof.

Here, a defective product, among tablets, is discharged to the defective product outlet 53 by the air sprayer 51, and a satisfactory product is transferred and discharged to the satisfactory product outlet 55 by a discharge section in communication with the atmospheric pressure or positive pressure region 22 formed in the second rotary unit 30.

Moreover, an inspection missed product, an inspection of which has been missed, among the tablets, is discharged through the inspection missed product outlet 52, and a defective product or a missing product, which is an inspection missed product, but which is not dropped, is discharged through the missing product outlet 56.

While the present disclosure has been particularly shown and described with reference to exemplary embodiments thereof, the present disclosure not limited thereto. It will be apparent to those skilled in the art that various changes and modifications thereof could be made within the spirit and scope of the present disclosure, and therefore it is to be understood that such changes and modifications belong to the scope of the appended claims.

The invention claimed is:

1. A tablet inspection apparatus comprising:
  a supply unit including a rotary plate inclinedly disposed, and a transfer plate having a downwardly inclined surface, inclined outwardly on the same level as top dead center of the rotary plate while rotating with the rotary plate around the rotary plate;
  a first rotary unit inclinedly disposed with respect to the supply unit, and formed such that suction force is applied in a certain section in a circumferential direction; and
  a second rotary unit installed on one side of the first rotary unit, and formed such that suction force is applied in a certain section in a circumferential direction,
  wherein the first rotary unit and the second rotary unit are arranged in the transverse direction and disposed inclinedly to each other, and an upper surface of the second rotary unit is inclinedly installed with respect to an upper surface of the first rotary unit,
  wherein the first rotary unit or the second rotary unit includes:
  a fixed disk in which a rotating shaft is installed to pass therethrough, forming a vacuum pressure area for applying vacuum pressure therein, and provided with a suction hole in communication with at least the vacuum pressure area; and
  a rotary disk combined with the rotating shaft and rotating, and in which a concave groove in communication with the vacuum pressure area is formed in a circumferential surface,
  wherein the rotary disk is provided with an outer circumferential tip portion extended toward the fixed disk to form an extended portion, the extended portion is provided with the concave groove formed therein, and both sides of an opening of the concave groove are provided with seating members formed of elastic materials, opposing each other, and attached thereto,
  wherein, in the first rotary unit, the concave groove is disposed in an upper surface of the extended portion, and a plane, defined by both tips of the opening of the concave groove, or a plane, defined by both upper surfaces of the seating members, forms the same plane as the downwardly inclined surface of the transfer plate,
  wherein a plane, defined by both tips of the opening of the concave groove of the first rotary unit, and a plane, defined by both tips of an opening of a concave groove of the second rotary unit, are disposed parallel to each other, and, in the second rotary unit, the concave groove is disposed on an inclined surface in the lower portion of the extended portion, the inclined surface facing the plane of the first rotary unit.

2. The tablet inspection apparatus of claim 1, wherein, in the fixed disk, a portion of a remaining area, to which vacuum pressure is not applied, is surrounded by a blocking block, and is in communication with ambient air or is connected to an external air spraying device, such that an atmospheric pressure or positive pressure region, to which atmospheric pressure or positive pressure is applied, is formed.

3. The tablet inspection apparatus of claim 1, wherein the same plane has an angle of inclination of 20° to 40° with respect to a horizontal plane.

4. The tablet inspection apparatus of claim 1, further comprising a discharge unit disposed in a lower portion of one side of the second rotary unit,
  wherein the discharge unit includes at least one air sprayer, at least one defective product outlet, and a satisfactory product outlet.

5. The tablet inspection apparatus of claim 4, wherein the air sprayer is installed through a medium of a separate support bracket near the second rotary unit.

6. The tablet inspection apparatus of claim 4, wherein the discharge unit further includes an inspection missed product outlet for discharging an inspection missed product transferred by the second rotary unit due to lack of determination of pass and fail of an appearance of a tablet.

7. The tablet inspection apparatus of claim 4, wherein the discharge unit further includes a missing product outlet for discharging a missing product, which is a defective product or an inspection missed product but which is being transferred by the second rotary unit.

* * * * *